US011692979B2

(12) United States Patent
Puthuvelil

(10) Patent No.: US 11,692,979 B2
(45) Date of Patent: Jul. 4, 2023

(54) SYSTEMS AND METHODS FOR THE DIRECT MEASUREMENT OF GLUTARALDEHYDE BASED BIOCIDE CONCENTRATION IN SEAWATER

(71) Applicant: Saudi Arabian Oil Company, Dhahran (SA)

(72) Inventor: Joseph Joseph Puthuvelil, Udhailiyah (SA)

(73) Assignee: Saudi Arabian Oil Company, Dhahran (SA)

( * ) Notice: Subject to any disclaimer, the term of this patent is extended or adjusted under 35 U.S.C. 154(b) by 381 days.

(21) Appl. No.: 16/990,414

(22) Filed: Aug. 11, 2020

(65) Prior Publication Data
US 2022/0050089 A1 Feb. 17, 2022

(51) Int. Cl.
| | |
|---|---|
| *G01N 33/18* | (2006.01) |
| *B01J 20/281* | (2006.01) |
| *G01N 30/16* | (2006.01) |
| G01N 30/02 | (2006.01) |
| B01J 20/292 | (2006.01) |

(52) U.S. Cl.
CPC .............. *G01N 30/48* (2013.01); *G01N 30/16* (2013.01); *G01N 33/18* (2013.01); *B01J 20/292* (2013.01); *G01N 2030/027* (2013.01)

(58) Field of Classification Search
CPC ........ G01N 30/48; G01N 33/18; G01N 30/16; G01N 2030/027; G01N 30/88; G01N 2030/8886; G01N 30/50; G01N 33/1826; G01N 30/34; G01N 2030/884; G01N 30/06; B01J 20/292

USPC .............. 73/61.52, 61.53, 61.55–61.57, 866; 422/70; 166/250.01, 252.1, 252.2, 252.3, 166/252.4

See application file for complete search history.

(56) References Cited

U.S. PATENT DOCUMENTS

| | | | |
|---|---|---|---|
| 9,772,287 | B2 | 9/2017 | Al-Moniee et al. |
| 2019/0079061 | A1 | 3/2019 | Unnerstall et al. |

FOREIGN PATENT DOCUMENTS

| | | |
|---|---|---|
| CN | 108362803 A | 8/2018 |
| CN | 108918707 A | 11/2018 |

OTHER PUBLICATIONS

International Search Report and Written Opinion for International Application No. PCT/US2021/045594, report dated Nov. 29, 2021; pp. 1-20.
Barnes, A.R.; "Determination of glutaraldehyde in solution and its bis-2,4-dinitrophenylhydrazone derivative determination of geometrical isomer ratios" Pharmaceutica Acta Helvetiae 68 (1993); pp. 113-119.

(Continued)

*Primary Examiner* — Robert R Raevis
(74) *Attorney, Agent, or Firm* — Bracewell LLP; Constance G. Rhebergen; Brian H. Tompkins

(57) ABSTRACT

The measurement of glutaraldehyde-based biocides in seawater without the use of a derivatization agent. The measurement of glutaraldehyde-based biocides in seawater may be performed without additional components to reduce background interferences. The concentration of a glutaraldehyde-based biocides in a seawater sample is determined using reversed phase liquid chromatography and a gradient mobile phase of acetonitrile and deionized water. Systems for determining the concentration of glutaraldehyde-based biocide in a seawater injection system are also provided.

25 Claims, 1 Drawing Sheet

(56) References Cited

OTHER PUBLICATIONS

Downs, Robert A. et al.; "Determination of the Biocide Econea in Artificial Seawater by Solid Phase Extraction and High Performance Liquid Chromatography Mass Spectrometry" Separations 2017, 4, 34; pp. 1-7.

Koivusalmi, Eija et al.; "Quantitative RP-HPLC Determination of Some Aldehydes and Hydroxyaldehydes as Their 2,4-Dinitrophenylhydrazone Derivatives" Analytical Chemistry, vol. 71, No. 1, Jan. 1, 1999; pp. 86-91.

Maggadani, Harmita et al.; "High-Performance Liquid Chromatography Analytical Method Validation for Glutaraldehyde and Benzalkonium Chloride in Disinfectants" International Journal of Applied Pharmaceutics, vol. 10, Special Issue 1, 2018; pp. 1-4.

Menet, M.-C. et al.; "Fast specific separation and sensitive quantification of bactericidal and sporicidal aldehydes by high-performance liquid chromatography: example of glutaraldehyde determination" Journal of Chromatography B, 692 (1996); pp. 79-86.

Takeda, Kazuhiko et al.; "Rapid and Highly Sensitive Determination of Low-Molecular-Weight Carbonyl Compounds in Drinking Water and Natural Water by Preconcentration HPLC with 2,4-Dinitrophenylhydrazine" Analytical Sciences, Dec. 2006, vol. 22; pp. 1509-1514.

Tsai, Chia-Fen et al.; "Determination of Low-molecule-weight Aldehydes in Packed Drinking Water by High Performance Liquid Chromatography" Journal of Food and Drug Analysis, vol. 11, No. 1, 2003; pp. 46-52.

Van Hoof, F. et al.; "Determination of Aliphatic Aldehydes in Waters by High-Performance Liquid Chromatography" Analytica Chimica Acta, 169 (1985); pp. 419-424.

Wang, Wenli et al.; "A novel method for trace aldehyde determination in foodstuffs based on fluorescence labeling by HPLC with fluorescence detection and mass spectrometric identification" Food Anal. Methods (2014) 7; pp. 1546-1556.

SYSTEMS AND METHODS FOR THE DIRECT MEASUREMENT OF GLUTARALDEHYDE BASED BIOCIDE CONCENTRATION IN SEAWATER

BACKGROUND

Field of the Disclosure

The present disclosure generally relates to the determination of the presence and concentration of biocides. More specifically, embodiments of the disclosure relate to measuring the concentration of glutaraldehyde-based biocides without the use of a derivatization agent.

Description of the Related Art

Seawater injection is a technique used in hydrocarbon production to increase the pressure of a hydrocarbon reservoir via waterflooding and ultimately increase production from a well. However, such waterflooding systems provide an ideal environment for the growth and proliferation of bacteria. In some instances, oxygen is removed from the water before injection to minimize equipment corrosion; however, the removal of oxygen may compound biofouling caused by anaerobic bacteria and provide an optimal environment for the growth of sulfate reducing bacteria (SRB) in biofilms. The biofouling and bacteria growth may occur on both the injection side and producing side of the waterflooding operation. The metabolic activity of the bacteria can lead to accelerated corrosion rates, plugging of filters, and eventual souring of the formation due to hydrogen sulfide.

SUMMARY

Seawater injection systems may be treated with biocides to control the growth of bacteria and resulting biofouling. The main objective of biocide treatment is to inhibit the growth and activity of sessile bacteria such as SRB. Glutaraldehyde (1,5-pentanedial) based biocides are typically used but large concentrations are required for the effective control over the bacteria. Glutaraldehyde-based biocides are also water soluble and partition more than 80% in the water phase. As such biocides are not inert, they are typically consumed or degraded under normal operating conditions. Consequently, periodic sampling of the biocide is performed to ensure optimal system performance and reduction or elimination of bacteria populations and biofouling.

Existing biocide sampling and measurement techniques require the use of a derivatization agent to fix the glutaraldehyde in the aqueous system. However, these techniques are time-consuming as they require sufficient reaction time to complete the derivatization reaction and obtain the results. Additionally, existing biocide sampling and measurement techniques also require the use of additional components to overcome background interferences (such as a buffer to maintain the pH).

In one embodiment, a method for determining a concentration of glutaraldehyde-based biocide in seawater. The method includes obtaining a sample of seawater from a seawater injection system and injecting the seawater sample into a reversed phase liquid chromatography (RP-LC) column using a gradient mobile phase having deionized water and acetonitrile to elute eluting glutaraldehyde from the column. The method also includes quantifying, based on the eluting, the glutaraldehyde-based biocide to determine the concentration, such that the injecting is performed without a derivatization agent.

In some embodiments, the injecting is performed without a pH buffer. In some embodiments, the gradient mobile phase consists of deionized water and acetonitrile. In some embodiments, the gradient mobile phase includes an initial composition of 90% deionized water and 10% acetonitrile. In some embodiments, the gradient mobile phase includes a final composition of 90% ultrapure water and 10% acetonitrile. In some embodiments, the deionized water includes ultrapure water. In some embodiments, the RP-LC column has an inner diameter (ID) of 4.6 mm, a length of 150 mm, and a particle size of 4 µm.

In another embodiment, a system for determining the concentration of a glutaraldehyde-based biocide in a seawater injection system. The system includes a sampling line having an inlet in fluid communication with a sampling point of a seawater an outlet, a sample reservoir connected to the outlet of the sampling line and configured to receive a seawater sample from the seawater injection system, and a sample metering pump having an inlet in fluid communication with the sample reservoir and an outlet. The system also includes a reversed phase liquid chromatography (RP-LC) column in fluid communication with the outlet of the sample metering pump and configured to receive the seawater sample from the sample metering pump. The reversed phase liquid chromatography (RP-LC) column includes a gradient mobile phase and operational to elute glutaraldehyde from the column using the gradient mobile phase and quantify the eluted glutaraldehyde, such that the gradient mobile phase includes deionized water and acetonitrile and the RP-LC column is operational without a derivatization agent in the seawater sample.

In some embodiments, the RP-LC column is operational without a pH buffer in the seawater sample. In some embodiments, the gradient mobile phase consists of deionized water and acetonitrile. In some embodiments, the gradient mobile phase having an initial composition of 90% deionized water and 10% acetonitrile. In some embodiments, the gradient mobile phase has a final composition of 90% ultrapure water and 10% acetonitrile. In some embodiments, the eluting is performed over a time period of 20 minutes. In some embodiments, the gradient mobile phase has a composition of 10% ultrapure water and 90% acetonitrile at 15 minutes of the time period. In some embodiments, the deionized water is ultrapure water. In some embodiments, the RP-LC column has an inner diameter (ID) of 4.6 mm, a length of 150 mm, and a particle size of 4 µm.

In another embodiment, a method for determining a concentration of glutaraldehyde in an aqueous salt solution. The method includes obtaining a sample of aqueous salt solution and injecting the sample into a reversed phase liquid chromatography (RP-LC) column. The method also includes eluting the glutaraldehyde from the column using a gradient mobile phase having deionized water and acetonitrile, the gradient mobile phase having an initial composition of 90% deionized water and 10% acetonitrile. The method further includes quantifying the eluted glutaraldehyde to determine the concentration, such that the injecting is performed without a derivatization agent. In some embodiments, the injecting is performed without a pH buffer. In some embodiments, the gradient mobile phase consists of deionized water and acetonitrile. In some embodiments, the aqueous salt solution is seawater. In some embodiments, the gradient mobile phase has a final composition of 90% ultrapure water and 10% acetonitrile. In some embodiments, the eluting is performed over a time period of 20 minutes. In some embodiments, the gradient mobile phase has a composition of 10% ultrapure water and 90% acetonitrile at 15 minutes of the time period. In some embodiments, the deionized water is ultrapure water. In some embodiments, the RP-LC column has an inner diameter (ID) of 4.6 mm, a length of 150 mm, and a particle size of 4 µm.

DETAILED DESCRIPTION

Figure 1:
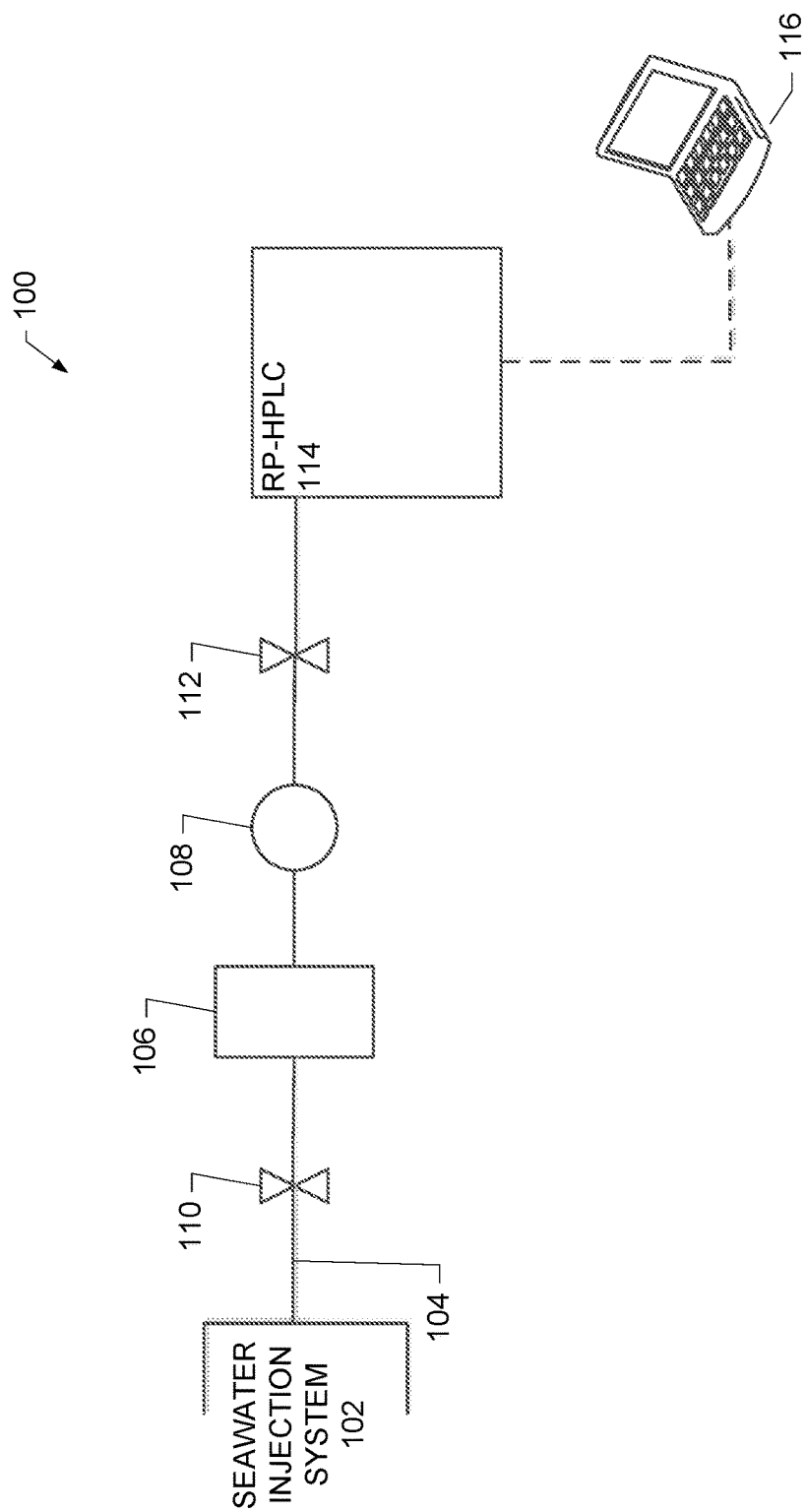
FIG. 1 is schematic diagram of a system for determining the concentration of glutaraldehyde-based biocide in a seawater injection system in accordance with an embodiment of the disclosure.

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure are directed to the measurement of glutaraldehyde (for example, glutaraldehyde-based biocides) in aqueous salt solutions (such as seawater) using reversed phase liquid chromatography (RP-LC) and without the use of a derivatization agent. In some embodiments, the measurement of glutaraldehyde in aqueous salt solutions may be performed without additional components to reduce background interferences. For example, the measurement of glutaraldehyde may be performed without a buffer to maintain the pH. Measuring the glutaraldehyde may include determining the concentration of glutaraldehyde in the aqueous salt solution. As used herein, the term RP-LC may include reversed phase high performance liquid chromatography (RP-HPLC) and may also include reversed high performance liquid chromatography equipped with diode array detection (HPLC-DAD).

Embodiments of the disclosure include the measurement of glutaraldehyde-based biocides in seawater. As will be appreciated, the measurement of glutaraldehyde may be indicative of the concentration of a glutaraldehyde-based biocide having a proportional amount of glutaraldehyde with other components.

Embodiments of the disclosure include a process for determining the concentration of a glutaraldehyde-based biocides in a seawater sample using a reversed phase liquid chromatograph (RP-LC) procedure. The process includes obtaining a sample of seawater having the glutaraldehyde-based biocides. The sample is injected into a reversed phase liquid chromatography (RP-LC) apparatus having a gradient mobile phase of acetonitrile and deionized water (in some embodiments, ultrapure water may be used). In some embodiments, the gradient mobile phase may vary between 10% by volume ultrapure water and 90% by volume acetonitrile to 90% by volume ultrapure water and 10% by volume acetonitrile. In some embodiments, the gradient mobile phase may vary over at time period of 20 minutes. In such embodiments, an example gradient is shown in Table 1:

TABLE 1

RP-LC MOBILE PHASE CONCENTRATION GRADIENT

| Elapsed Time | Gradient |
|---|---|
| 0 minutes | 90% deionized water 10% acetonitrile |
| 15 minutes | 10% deionized water 90% acetonitrile |
| 16 minutes | 90% deionized water 10% acetonitrile |
| 20 minutes | 90% deionized water 10% acetonitrile |

In some embodiments, ultrapure water used in the gradient mobile phase may have the parameters shown in Table 2:

TABLE 2

PARAMETERS OF ULTRAPURE WATER

| Parameter | Value |
|---|---|
| Resistivity | >18 MΩ · cm |
| Conductivity | ≤0.1 µS/cm |
| Total Organic Carbon (TOC) | ≤1 µg/L |
| Particles | No particles with size > 0.22 µm |
| Bacteria | <0.01 CFU/mL |
| Cations ($Li^+$, $Na^+$, $NH_4^+$, $K^+$, $Mg^{2+}$, $Mn^{2+}$, $Ca^{2+}$) | ≤2 µg/L |
| Anions ($F^-$, Lactate, Acetate, Formate, $Cl^-$, $NO_2^-$, $Br^-$, $NO_3^-$, $SO_4^{2-}$, $PO_4^{3-}$, $I^-$, Malonate, Oxalate) | ≤6 µg/L |

The process described in the disclosure and the determination of the concentration of a glutaraldehyde-based biocides in a seawater sample using reversed phase liquid chromatograph procedure is performed without a derivatization agent or reaction. For example, the RP-LC injection may consist of the seawater sample and the ultrapure water and acetonitrile mobile phase without any other components. In some embodiments, the process described in the disclosure and the determination of the concentration of a glutaraldehyde-based biocides in a seawater sample using RP-LC procedure is performed without any components to reduce background interferences, such as buffer to maintain the pH of the sample.

In some embodiments, the RP-LC apparatus may have an inner diameter (ID) of 4.6 mm, a length of 150 mm, and a particle size of 4 µm. In some embodiments, the RP-LC procedure may be performed at a temperature of 25° C. at a flowrate of 0.65 ml/min. In some embodiments, the RP-LC apparatus includes diode array detection. In other embodiments, other RP-LC apparatus may be use having different parameters may be used, and the process may be conducted at different temperatures and flowrates. In some embodiments, the RP-LC apparatus is an Agilent 1290 Infinity II LC and the column is an Agilent Poroshell 120 EC-C18 manufactured by Agilent Technologies, Inc. of Santa Clara, Calif., USA.

In some embodiments, a process for calibrating an RP-LC apparatus for the determination of glutaraldehyde in seawater is provided. The process includes obtaining a plurality of samples having standardized (that is, known) concentrations of biocide and determining the concentration of biocide in each sample using the technique described in the disclosure. The process includes determining a calibration curve based on the RP-LC results (for example, the area under the peak in the chromatogram) and the concentrations. A calibration coefficient (R), a limit of detection, and a limit of quantification, may also be determined.

Embodiments of the disclosure include a system for determining the concentration of glutaraldehyde-based biocide in a seawater injection system. As known in the art, the seawater injection system may be used to inject seawater into a well for waterflooding for enhance oil recovery (EOR) operations in hydrocarbon production.

The system described in the disclosure provides for the automatic (that is, without manual human operation) determination of the concentration of glutaraldehyde-based biocide. The determination may be an "online" determination, such that the seawater system may continue to operate while the determination is performed (that is, the seawater system is not taken "offline" for while the determination is performed).

FIG. 1 depicts a system 100 for determining the concentration of glutaraldehyde-based biocide in a seawater injection system 102 in accordance with an embodiment of the disclosure. The system 100 may include a sampling line 104, a sample reservoir 106, a sample pump 108, valves 110 and 112, and a RP-HPLC apparatus 114. The injection water sampling line 104 may be in fluid communication with a sampling point in a section of the seawater injection system 102. A sample of biocide containing seawater may be taking from the sampling point and through the valve 110 and stored in the sample reservoir 106. The system may include or be in wired or wireless communication with a remote computer 116 that controls and monitors the system.

The sample pump 108 and the valve 112 may obtain a predetermined quantity of seawater from the sample reservoir 106 and provide the quantity of seawater to the RP-LC apparatus 114. The RP-LC apparatus 114 may include reservoirs for ultrapure water and acetonitrile and may be configured to operate using the predetermined concentration gradient, such as the gradient described in Table 1 supra. The quantity of seawater is analyzed by the RP-LC apparatus 114 and the determined biocide concentration may be output from the RP-LC apparatus 114. For example, in some embodiments, the output from the RP-LC apparatus may be transmitted to a remote computer (for example, remote computer 116) for monitoring by a process control system or a human operator. The remote computer may be a desktop, a laptop, a smartphone, a tablet computer, or other computing device. In response to a received biocide concentration, a process control system or human operator may activate an alarm or other notification. In other instances, the process control system or a human operator may initiate the injection of additional biocide into a seawater injection system. In some embodiments, a seawater injection system may stop operation in response to the received biocide concentration.

EXAMPLES

The following examples are included to demonstrate embodiments of the disclosure. It should be appreciated by those of skill in the art that the techniques and compositions disclosed in the example which follows represents techniques and compositions discovered to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

An example measurement of glutaraldehyde based biocides was performed without a derivatization agent and without components to reduce background interferences.

The measurement was performed using an Agilent 1290 Infinity II LC System manufactured by Agilent Technologies, Inc. of Santa Clara, Calif., USA. The Agilent 1290 Infinity II LC System included the following modules: an Agilent 1290 Infinity II Multi-sampler; an Agilent 1290 Infinity II Multicolumn Thermostat; and an Agilent 1290 Infinity II Diode Array Detector equipped with a 10-mm Max-Light cartridge cell, all manufactured by Agilent Technologies, Inc. The columns used in the measurement was an Agilent Poroshell 120 EC-C18, 4.6×150 mm, 4 μm (that is a column having an inner diameter (ID) of 4.6 mm, a length of 150 mm, and a particle size of 4 μm) manufactured by Agilent Technologies, Inc. The software used during the experiments was Agilent OpenLAB LC series manufactured by Agilent Technologies, Inc.

The mobile phase for the reversed phase liquid chromatography was a combination of two solvents: acetonitrile and Milli-Q® water (ultrapure water produced by a Milli-Q system manufactured by MilliporeSigma of Burlington, Mass., USA. The experiment used a gradient mobile phase between 90% Milli-Q® water and 10% acetonitrile to 10% Milli-Q® water and 90% acetonitrile over a time period of 20 minutes. The flow rate for the RP-LC was about 0.65 milliliters per minute (ml/min) at a column temperature of 25° C. The parameters for the RP-LC experiment are summarized in Table 3:

TABLE 3

| RP-LC PARAMETERS | |
|---|---|
| Parameter | Value |
| Column | Agilent Poroshell 120 EC-C18, 4.6 × 150 mm, 4 μm |
| Mobile phase | Water and Acetonitrile |
| Gradient | 0 minutes-90% ultrapure Water 10% Acetonitrile. |
| | 15 minutes-10% ultrapure Water, 90% Acetonitrile. |
| | 16 minutes-90% ultrapure Water 10% Acetonitrile. |
| | 20 minutes-90% ultrapure Water 10% Acetonitrile. |
| Stop time | 20 minutes |
| Post time | 2 minutes |
| Flow rate | 0.65 mL/min |
| Injection volume | 99 μL from stock solution, at 25° C., draw speed 200 μL/min, eject speed 400 μL/m, 10 seconds needle wash |
| Column temperature | 25° C. |
| Detection | 235 nm, ref. wavelength 360, reference bandwidth 100, 10 Hz |

Three trials were run and the measured concentration of glutaraldehyde was compared to a standardized measurement in the seawater. Table 4 depicts the results of the three trials for various concentrations of glutaraldehyde as compared to the standardized measurement (in parts-per-million (ppm)) with the standard deviation and relative standard deviation:

TABLE 4

| RESULTS OF RP-LC TRIALS FOR GLUTARALDEHYDE CONCENTRATIONS | | | | | |
|---|---|---|---|---|---|
| STD ppm | Trial-1 | Trial-2 | Trial-3 | Std. Dev. | RSD (%) |
| 7.81 | 7.97 | 8.02 | 7.91 | 0.055 | 0.69 |
| 15.63 | 15.85 | 15.99 | 15.79 | 0.103 | 0.65 |
| 31.25 | 31.72 | 31.89 | 31.79 | 0.085 | 0.27 |
| 62.5 | 61.93 | 61.84 | 61.99 | 0.075 | 0.12 |
| 125 | 124.1 | 124.6 | 123.98 | 0.329 | 0.26 |
| 250 | 249.1 | 251.2 | 250.8 | 1.115 | 0.45 |
| 500 | 500.21 | 501.37 | 500.91 | 0.584 | 0.12 |

An average of the three trials was calculated and compared to the standardized measurement to further illustrate the accuracy of the glutaraldehyde measurements. Table 5 depicts the absolute error between the standardized measurement and determined average measurement (in ppm):

TABLE 5

ABSOLUTE ERROR FOR RP-LC TRIALS FOR GLUTARALDEHYDE CONCENTRATIONS

| STD ppm | Result ppm | Error |
| --- | --- | --- |
| 7.81 | 7.96 | −0.15 |
| 15.63 | 15.88 | −0.25 |
| 31.25 | 31.80 | −0.55 |
| 62.5 | 61.92 | 0.58 |
| 125 | 124.3 | 0.70 |
| 250 | 250.36 | −0.36 |
| 500 | 500.83 | −0.83 |

The experiments further established various analytical conditions for the determination of glutaraldehyde in seawater, including the sensitivity and linearity of the determination. The parameters of the calibration curve for glutaraldehyde concentrations between 1 mg/L and 500 mg/L were determined. Based on the experiments, the correlation coefficient (R) was 0.99, the limit of detection was 1.0 mg/L and the quantification limit was 3 mg/L.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method for determining a concentration of glutaraldehyde-based biocide in seawater, comprising:
    obtaining a sample of seawater from a seawater injection system;
    injecting the seawater sample into a reversed phase liquid chromatography (RP-LC) column comprising a gradient mobile phase comprising deionized water and acetonitrile to elute glutaraldehyde from the column;
    quantifying, based on the eluting, the glutaraldehyde-based biocide to determine the concentration, wherein the injecting is performed without a derivatization agent.

2. The method of claim 1, wherein the injecting is performed without a pH buffer.

3. The method of claim 1, wherein the gradient mobile phase consists of deionized water and acetonitrile.

4. The method of claim 1, wherein the gradient mobile phase comprises an initial composition of 90% deionized water and 10% acetonitrile.

5. The method of claim 1, wherein the gradient mobile phase comprises a final composition of 90% ultrapure water and 10% acetonitrile.

6. The method of claim 1, wherein the deionized water comprises ultrapure water.

7. The method of claim 1, wherein the RP-LC column has an inner diameter (ID) of 4.6 mm, a length of 150 mm, and a particle size of 4 μm.

8. A system for determining the concentration of a glutaraldehyde-based biocide in a seawater injection system;
    a sampling line having an inlet in fluid communication with a sampling point of a seawater injection system;
    a sample reservoir connected to the outlet of the sampling line and configured to receive a seawater sample from the seawater injection system;
    a sample metering pump having an inlet in fluid communication with the sample reservoir and an outlet;
    a reversed phase liquid chromatography (RP-LC) column in fluid communication with the outlet of the sample metering pump and configured to receive the seawater sample from the sample metering pump, the reversed phase liquid chromatography (RP-LC) column comprising a gradient mobile phase and operational to elute glutaraldehyde from the column using the gradient mobile phase and quantify the eluted glutaraldehyde, wherein the gradient mobile phase comprises deionized water and acetonitrile and the RP-LC column is operational without a derivatization agent in the seawater sample.

9. The system of claim 8, wherein the RP-LC column is operational without a pH buffer in the seawater sample.

10. The system of claim 8, wherein the gradient mobile phase consists of deionized water and acetonitrile.

11. The system of claim 8, wherein the gradient mobile phase comprises an initial composition of 90% deionized water and 10% acetonitrile.

12. The system of claim 8, wherein the gradient mobile phase comprises a final composition of 90% ultrapure water and 10% acetonitrile.

13. The system of claim 8, wherein the reversed phase liquid chromatography (RP-LC) column is operational to elute glutaraldehyde over a time period of 20 minutes.

14. The system of claim 13, wherein the gradient mobile phase comprises a composition of 10% ultrapure water and 90% acetonitrile at 15 minutes of the time period.

15. The system of claim 8, wherein the deionized water comprises ultrapure water.

16. The system of claim 8, wherein the RP-LC column has an inner diameter (ID) of 4.6 mm, a length of 150 mm, and a particle size of 4 μm.

17. A method for determining a concentration of glutaraldehyde in an aqueous salt solution, comprising:
    obtaining a sample of aqueous salt solution;
    injecting the sample into a reversed phase liquid chromatography (RP-LC) column;
    eluting the glutaraldehyde from the column using a gradient mobile phase comprising deionized water and acetonitrile, the gradient mobile phase comprising an initial composition of 90% deionized water and 10% acetonitrile; and quantifying the eluted glutaraldehyde to determine the concentration, wherein the injecting is performed without a derivatization agent.

18. The method of claim 17, wherein the injecting is performed without a pH buffer.

19. The method of claim 17, wherein the gradient mobile phase consists of deionized water and acetonitrile.

20. The method of claim 17, wherein the aqueous salt solution comprises seawater.

21. The method of claim 17, wherein the gradient mobile phase comprises a final composition of 90% ultrapure water and 10% acetonitrile.

22. The method of claim 17, wherein the eluting is performed over a time period of 20 minutes.

23. The method of claim 22, wherein the gradient mobile phase comprises a composition of 10% ultrapure water and 90% acetonitrile at 15 minutes of the time period.

24. The method of claim 17, wherein the deionized water comprises ultrapure water.

25. The method of claim 17, wherein the RP-LC column has an inner diameter (ID) of 4.6 mm, a length of 150 mm, and a particle size of 4 μm.

* * * * *